United States Patent
Kokin et al.

(10) Patent No.: US 7,772,443 B2
(45) Date of Patent: Aug. 10, 2010

(54) IODINE-CONTAINING FLUOROPOLYETHER AND PROCESS FOR PRODUCING THE SAME

(75) Inventors: Keisuke Kokin, Ibaraki (JP); Kimihiko Urata, Ibaraki (JP); Takehiro Sonoi, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 241 days.

(21) Appl. No.: 11/921,343

(22) PCT Filed: May 22, 2006

(86) PCT No.: PCT/JP2006/310116

§ 371 (c)(1),
(2), (4) Date: Nov. 30, 2007

(87) PCT Pub. No.: WO2006/129507

PCT Pub. Date: Dec. 7, 2006

(65) Prior Publication Data

US 2009/0048469 A1  Feb. 19, 2009

(30) Foreign Application Priority Data

May 30, 2005 (JP) ............................. 2005-156770

(51) Int. Cl.
*C07C 43/12* (2006.01)
(52) U.S. Cl. ...................... 568/677; 568/676
(58) Field of Classification Search .................. None
See application file for complete search history.

(56) References Cited

FOREIGN PATENT DOCUMENTS

| JP | 05-194298 | * | 8/1993 |
| JP | 05-331089 | | 12/1993 |
| JP | 06-016586 | | 1/1994 |
| JP | 2004-051595 | | 2/2004 |

OTHER PUBLICATIONS

Masayuki et al. (Patent abstract and computer generated English Translation of 05-294881, published Nov. 1993.*
n-Hexadecyl Iodide, Organic Syntheses II, pp. 322-323, 399-403 (1943) Terminally Perfluorinated Long-Chain Alkanethiols, J. of Fluorine Chemistry, pp. 107-115 (1999), vol. 93.
1-Iodo-Polyfluoroalkanes from Polyfluoroalkoxy Trimethylsilanes and Iodochloro Triphenylphorane, Tetrahedron Letter 35, pp. 1941-1944 (1994) Effect of a Perfluoroalkyl Group on the Elimination and Substitution Reactions of Two Homologous Series of Perfluoroalkyl-Substituted Iodoalkanes 49, pp. 2361-2369 (1984), J. Org. Chem.

* cited by examiner

*Primary Examiner*—Rosalynd Keys
(74) *Attorney, Agent, or Firm*—Brinks Hofer Gilson & Lione

(57) ABSTRACT

An iodine-containing fluoropolyether represented by the following general formula [I]:

$$RfO[CF(CF_3)CF_2O]_mCF(CF_3)(CH_2)_nI \qquad [I]$$

(where Rf is a perfluoroalkyl group having 1-3 carbon atoms, m is an integer of 0-10, and n is an integer of 3-12), is a novel compound having a perfluoropolyetheralkyl group capable of giving a flexibility to the molecule chain through the etheral bond, said perfluoropolyether alkyl group being bonded to the alkyl iodide having an alkyl group having 3 or more carbon atoms, and can be produced by reaction of a fluoropolyether group-containing alcohol represented by the following general formula [II]:

$$RfO[CF(CF_3)CF_2O]_mCF(CF_3)(CH_2)_nOH \qquad [II]$$

(Where Rf, m, and n have the same meanings as defined above) with a metal iodide, preferably potassium iodide.

5 Claims, No Drawings

IODINE-CONTAINING FLUOROPOLYETHER AND PROCESS FOR PRODUCING THE SAME

TECHNICAL FIELD

The present invention relates to an iodine-containing polyether and a process for producing the same, and more particularly to an iodine-containing fluoropolyether suitable for the industrial scale production and a process for producing the same.

BACKGROUND ART

General process for converting an alcoholic hydroxyl group to an iodide group so for reported includes the following ones.

$$RCH_2OH \rightarrow (RCH_2O)_3P \rightarrow RCH_2I \qquad (1)$$

In these series of reactions, phosphorus is initially used to produce trialkyl phosphite, which is then allowed to react with an iodine through an iodination reaction in the absence of a solvent at such a low reaction temperature as about 70° C. The process is industrially distinguished, but use of poisonous phosphorus, which is generally hard to handle, and also use of iodine make it difficult to select materials of reactor vessels, and hard to conduct mass production.

Non-Patent Literature 1: Org. Syn. II, 322-323, 399-403 (1943)

$$RCH_2OH \rightarrow RCH_2OSO_2R' \rightarrow RCH_2I \qquad (2)$$

In these series of reactions, reaction with $R'SO_2X$ is initially carried out, where not only a trapping agent (amine, etc.) is required for removing hydrogen halide produced during the sulfonic acid estrification reaction, but also potassium iodide is required for reaction of the resulting sulfonic acid ester; thus the process must be carried out in two steps, further requiring treatment of ammonium salt resulting from the reaction of hydrogen halide with amine, thus the process is industrially unpreferable.

Non-Patent Literature 2: J. Fluorine Chem. 93 107-115 (1999)

$$RCH_2OH \rightarrow RCH_2OSiR'_3 \rightarrow RCH_2I \qquad (3)$$

The process comprises two steps of reactions, i.e. reaction with $R'_3SiX$ and reaction with KI, and has a relatively high yield and a possibility of so-called one-pot synthesis, as industrial merits, but has such a demerit as causing a large amounts of hard-to-treat silicone-containing aqueous waste liquor.

Non-Patent Literature 3: Tetrahedron Letters 35, 1941-1944(1994)

$$RCH_2OH \rightarrow RCH_2I \qquad (4)$$

The process has a possibility of so-called one-pot synthesis, where available reagents are phosphoric acid anhydride and alkali metal iodide, and thus has industrial merits, but yield is as low as about 70%. That is, a higher yield is still desired for the industrial scale production.

Non-Patent Literature 4: J. Org. Chem. 49 2361-2368 (1984)

The group R in the compounds having an alcoholic hydroxyl group as used in these reactions (1)-(4) is an alkyl group or a perfluoroalkyl group, and there have been so far no examples showing use of fluoropolyetheralkyl group. Furthermore, iodine-containing fluoropolyethers represented by the following general formula [I] so far reported:

$$RfO[CF(CF_3)CF_2O]mCF(CF_3)(CH_2)nI \qquad [I]$$

have been limited to perfluoropolyetheralkylethyl iodides up to n=2, and there have been so far no examples reporting perfluoropolyetheralkylalkyl iodide of n≧3.

Patent Literature 1: JP-A-6-16586
Patent Literature 2: JP-A-5-331089

DISCLOSURE OF THE INVENTION

Problem to be Solved by the Invention

An object of the present invention is to provide a novel compound having a perfluoropolyetheralkyl group capable of giving a flexibility to the molecular chain through the etheral bond, the perfluoropolyetheralkyl group being bonded to an alkyl iodide whose alkyl group has 3 or more carbon atoms, and also to provide a process for producing the same.

Means for Solving the Problem

The present invention provides an iodine-containing fluoropolyether represented by the following general formula [I]:

$$RfO[CF(CF_3)CF_2O]mCF(CF_3)(CH_2)nI \qquad [I]$$

(where Rf is a perfluoroalkyl group having 1 to 3 carbon atoms, m is an integer of 0-10, and n is an integer of 3-12), which can be produced by reaction of a fluoropolyether group-containing alcohol represented by the following general formula [II]:

$$RfO[CF(CF_3)CF_2O]mCF(CF_3)(CH_2)nOH \qquad [II]$$

(where Rf, m, and n have the same meanings as defined above) with a metal iodide.

EFFECT OF THE INVENTION

The present iodine-containing fluoropolyether is a novel compound having a perfluoropolyetheralkyl group capable of giving a flexibility to the molecular chain through the etheral bond, the perfluoropolyetheralkyl group being bonded to an alkyl iodide whose alkyl group has 3 or more carbon atoms. The present novel compound is a so-called general-purpose compound as a starting material for various types of synthesis reaction. That is, different from the alkyl iodides or perfluoroalkylalkyl iodides reported in the afore-mentioned Non-Patent Literatures 1 to 4, the present novel compound has numbers of oxygen atoms in the molecule, which can give a flexibility to the molecule, and thus is expected to provide various function.

The present fluoropolyetheralkylalkyl iodide has a high reactivity and can be used as a fluoropolyether-alkylation reagent for making fluoropolyetheralkylalkyl metal iodides by a reaction with lithium or magnesium, or can be widely applied as industrial raw materials, etc. by replacement of the iodide group with other functional groups such as phosphorus atomic groups or sulfur atomic groups.

Limitation of number of carbon atoms to 3 or more in the alkyl group of alkyl iodide bonded to the perfluoropolyetheralkyl group has a merit in the addition reaction of a nucleophilic reagent, as compared with the conventional alkyl group having 2 or 1 carbon atom.

That is, in the bimolecular nucleophilic substitution reaction (Sn2 type substitution reaction) of perfluoropolyetheralkyl ethyl iodide, where number of carbon atoms of the alkyl group in the alkyl iodide is 2, with a nucleophilic reagent, the nucleophilic reagent acts not as a nucleophilic seed, but acts on the perfluoropolyetheralkyl ethyl iodide as a base, thereby causing a β-positioned hydrogen abstraction phenomenon by the iodine atom, and consequently causing an E2 elimination reaction (bimolecular elimination reaction), that is, a dehydroiodization reaction. Thus, it is difficult to obtain the desired compound under the ordinary conditions. Such a phenomenon can occurs owing to a higher acidity of the hydrogen atom adjacent to the fluorine atom.

On the other hand, by limitation of number of carbon atoms to 3 or more in the alkyl group of alkyl iodide the acidity of β-positioned hydrogen atom in relation to the iodine atom that takes part in the elimination reaction is considerably reduced owing to the presence of the hydrocarbon group between the perfluoropolyetheralkyl group and the iodide group, making the dehydroiodization reaction hard to take place, and consequently causing the Sn2 reaction to take place. Thus, it is possible to obtain the desired product.

Easy occurrence of Sn2 reaction means widening of a range of the desired compound design, resulting in a wider range of available means of acquisition for producing useful compounds.

By reaction of fluoropolyether group-containing alcohol corresponding to an iodine-containing fluoropolyether with a metal iodide, preferably potassium iodide in phosphoric acid, preferably phosphoric acid anhydride, the present process can produce an iodine-containing fluoropolyether of high purity in high yield such as 80% or more, without any disadvantage so far observed in the prior art.

BEST MODES FOR CARRYING OUT THE INVENTION

Fluoropolyether group-containing alcohol [II] for use as a starting material for iodine-containing fluoropolyether [I] can be obtained by reaction of a compound represented by the following general formula [III]:

RfO[CF(CF$_3$)CF$_2$O]$m$CF(CF$_3$)I    [III]

with an organic peroxide and then by reaction with an unsaturated alcohol represented by the following general formula [IV]:

CH$_2$=CH(CH$_2$)$n$OH    [IV], followed by a reduction reaction.

A metal iodide, preferably an alkali metal iodide, more preferably potassium iodide, can be used in an excess amount by mole, preferably about 2 to about 7 parts by mole, more preferably about 3 to about 7 parts by mole on the basis of one part by mole of the starting material [II].

Reaction between the starting material [II] and the metal iodide can be carried out in phosphoric acid. Phosphoric acid for use in the reaction is a readily available aqueous 85 wt. % phosphoric acid solution. That is, about 15 wt. % of water is contained therein, and thus at least 20 wt. % of P$_2$O$_5$, preferably 20-25 wt. % of P$_2$O$_5$ must be added to the aqueous 85-wt. % phosphoric acid solution to anhydrize the latter. When the amount of added P$_2$O$_5$ is smaller, the reaction system cannot be kept in a thoroughly anhydrous state, lowering the reaction conversion. That is, it is presumable that, when water is contained water in the system of high-temperature reaction, the substitution reaction between the resulting alkyl iodide [I] and water may take place again to undergo a back reaction of forming the starting alcohol material [II] again. To prevent such a back reaction, a sufficient amount of P$_2$O$_5$ must be added to the reaction system.

The reaction can be carried out by adding a sufficient amount of P$_2$O$_5$ to an aqueous phosphoric acid solution to prepare phosphoric acid anhydride, then adding potassium iodide thereto, and then dropwise adding fluoropolyether group-containing alcohol thereto, stirring the mixture at room temperature for an appropriate time after the dropwise addition, and then elevating the reaction temperature to about 100° to about 150° C., preferably 120°-140° C.

The lower the reaction temperature, the longer the reaction time. On the other hand, the higher the reaction temperature, the more promoted the decomposition of the reaction product or the afore-mentioned back reaction by the reaction with water. Thus, the reaction time takes about 24 to about 96 hours at the afore-mentioned reaction temperature. When the reaction time takes more than about 96 hours, the reaction conversion will be considerably lowered. Thus, it is preferable the reaction time must be kept within about 72 hours. Furthermore, prolonged reaction time is not preferable because of promotion of decomposition, etc.

After the reaction, an organic solvent such as R-225 (HCFC-225), etc. and water are added to the reaction mixture to separate an organic layer, and the separated organic layer is recovered and washed with an aqueous sodium thiosulfate solution and successively an aqueous saturated sodium chloride solution. Iodine resulting from the reaction is subjected to reduction treatment with sodium thiosulfate, the organic layer so further purified by distillation, after distilling off the organic solvent.

EXAMPLES

The present invention will be described in detail below, referring to Examples.

Example 1

55 g (0.39 moles) of P$_2$O$_5$ was slowly added to 277 g (2.40 moles) of 85 wt. % phosphoric acid charged into a 1,000 ml-capacity flask provided with a reflux condenser, a thermometer, and a stirrer in a nitrogen atmosphere, while cooling the flask, if required. Then, 484 g (2.91 mole) of potassium iodide was further slowly added thereto, followed by stirring at room temperature for one hour. Then, 300 g (99.5 GC %, 441 m mole) of the following compound was slowly dropwised added thereto at room temperature:

C$_3$F$_7$O[CF(CF$_3$)CF$_2$O]$_2$CF(CF$_3$)(CH$_2$)$_3$OH

After the dropwise addition, the mixture was vigorously stirred with heating at 130° C. for 72 hours, so as to prevent separation of the mixture into discrete layers, and then 200 ml of R-225 and 100 ml of water were added thereto to separate an organic layer. The organic layer was the recovered and washed with an aqueous 5 wt. % sodium thiosulfate, and successively with an aqueous saturated sodium chloride solution. By distilling off R-225 through an evaporator, 356.8 g (92.4 GC %, yield: 95%) of the corresponding 1-iodo-4,6,6,7,9,9,10,12,12,13,13,14,14,14-tetradecafluoro-4,7,10-tris (trifluoromethyl)-5,8,11-trioxatetradecane having the following chemical formula was obtained.

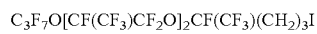

C$_3$F$_7$O[CF(CF$_3$)CF$_2$O]$_2$CF(CF$_3$)(CH$_2$)$_3$I 356 g of the resulting crude product was transferred into a flask provided with a Helipack No. 1-filled distillation column, 30 mm in diameter and 200 mm in length, and subjected to vacuum distillation to obtain 278 g (99.4 GC %, distillation yield: 84%) having a boiling point of 70°-71° C./100 Pa.

Example 2

60 g (0.42 moles) of P$_2$O$_5$ was slowly added to 300 g (2.62 moles) of 85 wt. % phosphoric acid charged in a 1,000 ml-capacity flask provided with a reflux condenser, a thermometer, and a stirrer in a nitrogen atmosphere, while cooling the flask, if required. 488 g (2.94 moles) of potassium iodide was further added thereto, followed by stirring at room temperature for one hour. Then, 314 g (99.0 GC %, 450 m moles) of the following compound was slowly dropwise added thereto at room temperature:

$C_3F_7O[CF(CF_3)CF_2O]_2CF(CF_3)(CH_2)_4OH$

After the dropwise addition, the mixture was vigorously stirred with heating at 130° C. for 72 hours, so as to prevent separation of the mixture into discrete layers, and then 200 ml of R-225 and 100 ml of water were added thereto to separate an organic layer. The organic layer was then recovered, and washed with an aqueous 5 wt. % sodium thiosulfate solution, and then with an aqueous saturated sodium chloride solution. By distilling off R-225 through an evaporator, 362.8 g (92.3 GC %, yield: 93%) of the corresponding 1-iodo-5,7,7,8,10, 10,11,13,13,14,14,15,15,15-tetradecafluoro-5,8,11-tris(trifluoromethyl)-6,9,12-trioxapentadecane having the following chemical formula was obtained.

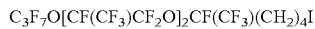

$C_3F_7O[CF(CF_3)CF_2O]_2CF(CF_3)(CH_2)_4I$ 360 g of the resulting crude product was transferred into a Helipack No. 1-filled distillation column, 30 mm in diameter and 200 mm in length, and subjected to vacuum distillation to obtain 263 g (98.1 GC %, distillation yield: 78%) of purified product having a boiling point of 75°-78° C./100 Pa.

The invention claimed is:

1. A process for producing an iodine-containing fluoropolyether represented by the following general formula [I]:

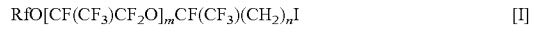

$$RfO[CF(CF_3)CF_2O]_mCF(CF_3)(CH_2)_nI \qquad [I]$$

where Rf is a perfluoroalkyl group having 1-3 carbon atoms, m is an integer of 0-10, and n is an integer of 3-12,
which process comprises allowing a fluoropolyether group-containing alcohol represented by the following general formula [II]:

$$RfO[CF(CF_3)CF_2O]_mCF(CF_3)(CH_2)_nOH \qquad [II]$$

where Rf is a perfluoroalkyl group having 1-3 carbon atoms, m is an integer of 0-10, and n is an integer of 3-12 to react with a metal iodide.

2. A process for producing an iodine-containing fluoropolyether to claim 1, wherein the metal iodide is potassium iodide.

3. A process for producing an iodine-containing fluoropolyether according to claim 1, wherein the iodization reaction is carried out in phosphoric acid.

4. A process for producing an iodine-containing fluoropolyether according to claim 3, wherein the phosphoric acid is phosphoric acid anhydride.

5. A process for producing an iodine-containing fluoropolyether according to claim 4, wherein the phosphoric acid anhydride is formed by adding $P_2O_5$ to phosphoric acid.

* * * * *